United States Patent
deLong et al.

(10) Patent No.: US 6,586,463 B2
(45) Date of Patent: Jul. 1, 2003

(54) $C_{16}$ UNSATURATED FP-SELECTIVE PROSTAGLANDINS ANALOGS

(75) Inventors: Mitchell Anthony deLong, West Chester, OH (US); David Lindsey Soper, Mason, OH (US); John August Wos, Cincinnati, OH (US); Biswanath De, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/946,021

(22) Filed: Sep. 4, 2001

(65) Prior Publication Data

US 2002/0037913 A1 Mar. 28, 2002

Related U.S. Application Data

(63) Continuation of application No. PCT/US00/05301, filed on Feb. 29, 2000.
(60) Provisional application No. 60/122,924, filed on Mar. 5, 1999.

(51) Int. Cl.[7] .................. C07C 405/00; A61K 31/5575
(52) U.S. Cl. ....................... 514/443; 514/530; 514/569; 514/570; 546/335; 548/170; 549/77; 549/58; 560/56; 560/60; 562/466; 562/469; 562/470
(58) Field of Search ...................... 560/60, 56; 514/443, 514/569, 570, 530; 546/335; 548/170; 549/58, 77; 562/466, 469, 470

(56) References Cited

U.S. PATENT DOCUMENTS

| | | | |
|---|---|---|---|
| 3,776,938 A | | 12/1973 | Sune et al. |
| 3,966,792 A | | 6/1976 | Hayashi et al. |
| 3,974,213 A | * | 8/1976 | Hess ........................... 514/530 |
| 3,984,424 A | * | 10/1976 | Schaff ........................ 514/530 |
| 4,011,262 A | | 3/1977 | Hess et al. |
| 4,024,179 A | | 5/1977 | Bindra et al. |
| 4,073,934 A | | 2/1978 | Skuballa et al. |
| 4,105,854 A | | 8/1978 | Gibson |
| 4,128,720 A | | 12/1978 | Hayashi et al. |
| 4,268,522 A | | 5/1981 | Eggler et al. |

FOREIGN PATENT DOCUMENTS

| | | | |
|---|---|---|---|
| DE | 2660990 | 7/1976 | |
| DE | 2517771 | * 10/1976 | .................. 514/530 |
| WO | WO 96/36599 A1 | 11/1996 | |
| WO | WO 97/23225 A1 | 7/1997 | |
| WO | WO 99/12550 A1 | 3/1999 | |
| WO | WO 99/12551 A1 | 3/1999 | |
| WO | WO 99/12895 A1 | 3/1999 | |
| WO | WO 99/12896 A1 | 3/1999 | |
| WO | WO 99/12899 A1 | 3/1999 | |

OTHER PUBLICATIONS

Collins et al., "Synthesis of Therapeutically Useful Prostaglandin and Prostacyclin Analogs", *Chemical Reviews*, 1993, pp. 1533–1564, vol. 93, No. 4.

Bundy et al., "Synthesis of 17–Phenyl–18,19,20–trinorprostaglandins I. The Pg, Series", *Prostaglandins*, 1975, pp. 1–4, vol. 9, No. 1.

Bartmann et al., "Synthesis and Biological Activity", *Prostaglandins*, 1979, pp. 301–311, vol. 17, No. 2.

Liljebris et al., "Derivatives of 17–Phenyl–18,19,20–trinorprostaglandin $F_{2\alpha}$ Isopropyl Ester: Potential Antigalucoma Agents", *J. Med. Chem.*, 1995, pp. 289–304, vol. 38. No. 2.

\* cited by examiner

Primary Examiner—Robert Gerstl
(74) Attorney, Agent, or Firm—David V. Upite; James C. Kellerman

(57) ABSTRACT

Compounds having the general structure:

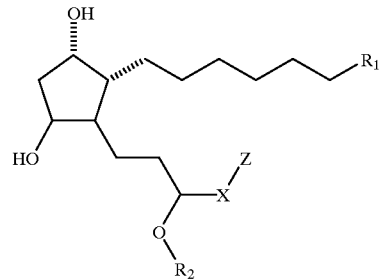

which are useful for the treatment of a variety of diseases and conditions, such as bone disorders.

18 Claims, No Drawings

$C_{16}$ UNSATURATED FP-SELECTIVE PROSTAGLANDINS ANALOGS

CROSS REFERENCE

This is a continuation under 35 U.S.C. §120 of PCT International Application Ser. No. PCT/US00/05301, filed Feb. 29, 2000; which claims priority to Provisional Application Ser. No. 60/122,924, filed Mar. 5, 1999.

TECHNICAL FIELD

The subject invention relates to certain novel analogs of the naturally occurring prostaglandins. Specifically, the subject invention relates to novel Prostaglandin F analogs. The subject invention further relates to methods of using said novel Prostaglandin F analogs. Preferred uses include methods of treating bone disorders and glaucoma.

BACKGROUND OF THE INVENTION

Naturally occurring prostaglandins (PGA, PGB, PGE, PGF, and PGI) are C-20 unsaturated fatty acids. $PGF_2$, the naturally occurring Prostaglandin F in humans, is characterized by hydroxyl groups at the $C_9$ and $C_{11}$ positions on the alicyclic ring, a cis-double bond between $C_5$ and $C_6$, and a trans-double bond between $C_{13}$ and $C_{14}$. Thus $PGF_2$ has the following formula:

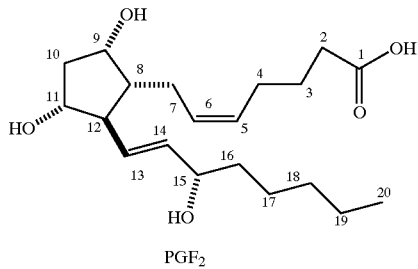

$PGF_2$

Analogs of naturally occurring Prostaglandin F have been disclosed in the art. For example, see U.S. Pat. No. 4,024,179 issued to Bindra and Johnson on May 17, 1977; German Patent No. DT-002,460,990 issued to Beck, Lerch, Seeger, and Teufel published on Jul. 1, 1976; U.S. Pat. No. 4,128,720 issued to Hayashi, Kori, and Miyake on Dec. 5, 1978; U.S. Pat. No. 4,011,262 issued to Hess, Johnson, Bindra, and Schaaf on Mar. 8, 1977; U.S. Pat. No. 3,776,938 issued to Bergstrom and Sjovall on Dec. 4, 1973; P. W. Collins and S. W. Djuric, "Synthesis of Therapeutically Useful Prostaglandin and Prostacyclin Analogs", *Chem. Rev.* Vol. 93 (1993), pp. 1533–1564; G. L. Bundy and F. H. Lincoln, "Synthesis of 17-Phenyl-18,19,20-Trinorprostaglandins: I. The $PG_1$ Series", *Prostaglandins*, Vol. 9 No. 1 (1975), pp. 1–4; W. Bartman, G. Beck, U. Lerch, H. Teufel, and B. Scholkens, "Luteolytic Prostaglandins: Synthesis and Biological Activity", *Prostaglandins*, Vol. 17 No. 2 (1979), pp. 301–311; C. liljebris, G. Selen, B. Resul, J. Stemschantz, and U. Hacksell, "Derivatives of 17-Phenyl-18,19,20-trinorprostaglandin $F_2\alpha$ Isopropyl Ester: Potential Antiglaucoma Agents", *Journal of Medicinal Chemistry*, Vol. 38 No. 2 (1995), pp. 289–304.

Naturally occurring prostaglandins are known to possess a wide range of pharmacological properties. For example, prostaglandins have been shown to: relax smooth muscle, which results in vasodilatation and bronchodilatation, to inhibit gastric acid secretion, to inhibit platelet aggregation, to reduce intraocular pressure, and to induce labor. Although naturally occurring prostaglandins are characterized by their activity against a particular prostaglandin receptor, they generally are not specific for any one prostaglandin receptor. Therefore, naturally-occurring prostaglandins are known to cause side effects such as inflammation, as well as surface irritation when administered systemically. It is generally believed that the rapid metabolism of the naturally occurring prostaglandins following their release in the body limits the effects of the prostaglandin to a local area. This effectively prevents the prostaglandin from stimulating prostaglandin receptors throughout the body and causing the effects seen with the systemic administration of naturally occurring prostaglandins.

Prostaglandins, especially prostaglandins of the E series (PGE), are known to be potent stimulators of bone resorption. $PGF_2$ has also been shown to be a stimulator of bone resorption but not as potent as $PGE_2$. Also, it has been demonstrated the $PGF_2$ has little effect on bone formation as compared to $PGE_2$. It has been suggested that some of the effects of $PGF_2$ on bone resorption, formation and cell replication may be mediated by an increase in endogenous $PGE_2$ production.

In view of both the wide range of pharmacological properties of naturally occurring prostaglandins and of the side effects seen with the systemic administration of these naturally occurring prostaglandins, attempts have been made to prepare analogs to the naturally occurring prostaglandins that are selective for a specific receptor or receptors. A number of such analogs have been disclosed in the art. Though a variety of prostaglandin analogs have been disclosed, there is a continuing need for potent, selective prostaglandin analogs for the treatment of a variety diseases and conditions.

SUMMARY OF THE INVENTION

The invention provides novel PGF analogs. In particular, the present invention relates to compounds having a structure according to the following formula:

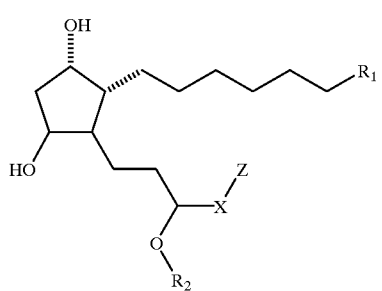

Formula A wherein $R_1$, $R_2$, X, and Z are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of a variety of diseases and conditions, such as bone disorders and glaucoma. Accordingly, the invention further provides pharmaceutical compositions comprising these compounds. The invention still further provides methods of treatment for bone disorders and glaucoma using theses compounds or the compositions containing them.

DETAILED DESCRIPTION OF THE INVENTION

Terms and Definitions

"Alkyl" is a saturated or unsaturated hydrocarbon chain having 1 to 18 carbon atoms, preferably I to 12, more preferably 1 to 6, more preferably still 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to 4 substituents. Preferred substituted alkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Lower alkyl" is an alkyl chain comprised of 1 to 6, preferably 1 to 3 carbon atoms.

"Aromatic ring" is an aromatic hydrocarbon ring. Aromatic rings are monocyclic or fused bicyclic ring systems. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring system. Bicyclic aromatic rings include ring systems wherein one ring in the system is aromatic. Preferred bicyclic aromatic rings are ring systems wherein both rings in the system are aromatic. Aromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred aromatic rings include naphthyl and phenyl. The most preferred aromatic ring is phenyl.

"Carbocyclic aliphatic ring" is a saturated or unsaturated hydrocarbon ring. Carbocyclic aliphatic rings are not aromatic. Carbocyclic aliphatic rings are monocyclic. Carbocyclic aliphatic rings contain from about 4 to about 10 carbon atoms, preferably from 4 to 7 carbon atoms, and most preferably from 5 to 6 carbon atoms in the ring. Carbocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1$–$C_{12}$; more preferred are $C_1$–$C_6$; more preferred still are $C_1$–$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to 4 substituents. Preferred substituted heteroalkyl are mono-, di-, or trisubstituted. The substituents may be lower alkyl, halo, hydroxy, aryloxy (e.g., phenoxy), acyloxy (e.g., acetoxy), carboxy, monocyclic aromatic ring (e.g., phenyl), monocyclic heteroaromatic ring, monocyclic carbocyclic aliphatic ring, monocyclic heterocyclic aliphatic ring, and amino.

"Lower heteroalkyl" is a heteroalkyl chain comprised of 1 to 6, preferably 1 to 3 member atoms.

"Heteroaromatic ring" is an aromatic ring containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings include ring systems wherein only one ring in the system is aromatic. Preferred bicyclic heteroaromatic rings are ring systems wherein both rings in the system are aromatic. Bicyclic heteroaromatic rings contain from 8 to 12 member atoms, preferably 9 or 10 in the ring. Heteroaromatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo, haloalkyl, and phenyl. Preferred monocyclic heteroaromatic rings include thienyl, thiazolo, purinyl, pyrimidyl, pyridyl, and furanyl. More preferred monocyclic heteroaromatic rings include thienyl, furanyl, and pyridyl. The most preferred monocyclic heteroaromatic ring is thienyl. Preferred bicyclic heteroaromatic rings include benzo[β]thiazolyl, benzo[β]thiophenyl, quinolinyl, quinoxalinyl, benzo[β]furanyl, benzimidizolyl, benzoxazolyl, indolyl, and anthranilyl. More preferred bicyclic heteroaromatic rings include benzo [β]thiazolyl, benzo [β]thiophenyl, and benzoxazolyl.

"Heteroatom" is a nitrogen, sulfur, or oxygen atom. Groups containing more than one heteroatom may contain different heteroatoms.

"Heterocyclic aliphatic ring" is a saturated or unsaturated ring containing carbon and from 1 to about 4 heteroatoms in the ring, wherein no two heteroatoms are adjacent in the ring and no carbon in the ring that has a heteroatom attached to it also has a hydroxyl, amino, or thiol group attached to it. Heterocyclic aliphatic rings are not aromatic. Heterocyclic aliphatic rings are monocyclic. Heterocyclic aliphatic rings contain from about 4 to about 10 member atoms (carbon and heteroatoms), preferably from 4 to 7 member atoms, and most preferably from 5 to 6 member atoms in the ring. Heterocyclic aliphatic rings may be unsubstituted or substituted with from 1 to 4 substituents on the ring. The substituents may be halo, cyano, alkyl, heteroalkyl, haloalkyl, phenyl, phenoxy or any combination thereof. Preferred substituents include halo and haloalkyl. Preferred heterocyclic aliphatic rings include piperzyl, morpholinyl, tetrahydrofuranyl, tetrahydropyranyl and piperdyl.

"Phenyl" is a monocyclic aromatic ring which may or may not be substituted with from about 1 to about 4 substituents. The substituents may be fused but not bridged and may be substituted at the ortho, meta or para position on the phenyl ring, or any combination thereof. The substituents may be halo, acyl, cyano, alkyl, heteroalkyl, haloalkyl, phenyl, phenoxy or any combination thereof. Preferred substituents on the phenyl ring include halo and haloalkyl. The most preferred substituent is halo. The preferred substitution pattern on the phenyl ring is ortho or meta. The most preferred substitution pattern on the phenyl ring is meta.

Compounds

The subject invention involves compounds having the following structure:

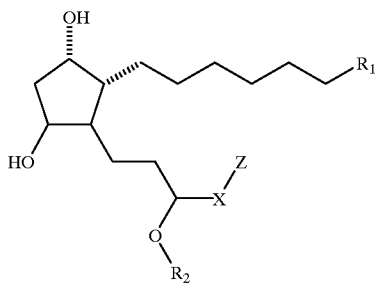

Formula A

In the above structure, $R_1$ is $CO_2H$, $C(O)NHOH$, $CO_2R_3$, $CH_2OH$, $S(O)_2R_3$, $C(O)NHR_3$, $C(O)NHS(O)_2R_4$, or tetrazole; wherein $R_3$ is alkyl, heteroalkyl, carbocyclic aliphatic ring, heterocyclic aliphatic ring, monocyclic aromatic ring, or monocyclic heteroaromatic ring; and $R_4$ is alkyl, heteroalkyl, carbocyclic aliphatic ring, heterocyclic aliphatic ring, monocyclic aromatic ring, or monocyclic heteroaromatic ring. Preferred $R_3$ is methyl, ethyl, and isopropyl. Preferred R, is $CO_2H$, $C(O)NHOH$, $CO_2R_3$, $C(O)NHS(O)_2R_4$, and tetrazole. Most preferred R, is $CO_2H$ and $CO_2R_3$.

In the above structure, $R_2$ is H or lower alkyl. The most preferred $R_2$ is H.

In the above structure, X is C≡C or a covalent bond.

In the above structure, Z is an aromatic ring or a heteroaromatic ring provided that when Z is a heteroaromatic ring and X is a covalent bond, Z is attached to $C_{15}$ via a Carbon member atom. When X is C≡C, preferred Z is monocyclic aromatic ring. When X is C≡C, more preferred Z is furanyl, thienyl, and phenyl. When X is a covalent bond, preferred Z is a bicyclic heteroaromatic ring.

The invention also includes optical isomers, diastereomers and enantiomers of the above structure. Thus, at all stereocenters where stereochemistry is not defined ($C_{11}$, $C_{12}$, and $C_{15}$), both epimers are envisioned. Preferred stereochemistry at all such stereocenters of the compounds of the invention mimic that of naturally occurring $PGF_2$.

As can be readily seen from the description above, the invention can be placed into two subgenuses based upon the functional group "X." Formula A1 (X is C≡C) and Formula A2 (X is a covalent bond) below depict these two subgenuses:

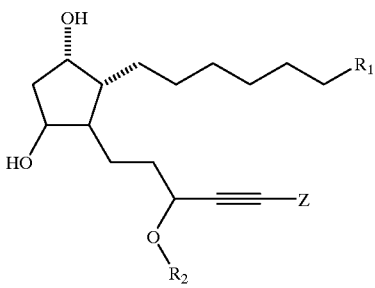

Formula A1

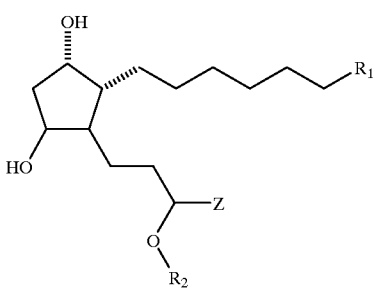

Formula A2

It has been discovered that the novel PGF analogs of the subject invention are useful for treating bone disorders, especially those that require a significant increase in bone mass, bone volume, or bone strength. Surprisingly, the compounds of the subject invention have been found to provide the following advantages over known bone disorder therapies: (1) An increase trabecular number through formation of new trabeculae; (2) An increase in bone mass and bone volume while maintaining a more normal bone turnover rate; and/or (3) An increase in bone formation at the endosteal surface without increasing cortical porosity.

In order to determine and assess pharmacological activity, testing of the subject compounds in animals is carried out using various assays known to those skilled in the art. For example, the bone activity of the subject compounds can be conveniently demonstrated using an assay designed to test the ability of the subject compounds to increase bone volume, mass, or density. An example of such assays is the ovariectomized rat assay.

In the ovariectomized rat assay, six-month old rats are ovariectomized, aged 2 months, and then dosed once a day subcutaneously with a test compound. Upon completion of the study, bone mass and/or density can be measured by dual energy x-ray absorptometry (DXA) or peripheral quantitative computed tomography (pQCT), or micro computed tomography (mCT). Alternatively, static and dynamic histomorphometry can be used to measure the increase in bone volume or formation.

Pharmacological activity for glaucoma can be demonstrated using assays designed to test the ability of the subject compounds to decrease intraocular pressure. Examples of such assays are described in the following reference, incorporated herein: C. liljebris, G. Selen, B. Resul, J. Sternschantz, and U. >Hacksell, "Derivatives of 17-Phenyl-18,19,20-trinorprostaglandin $F_2\alpha$ Isopropyl Ester: Potential Antiglaucoma Agents", *Journal of Medicinal Chemistry*, Vol. 38 No. 2 (1995), pp. 289–304.

Compounds useful in the subject invention can be made using conventional organic syntheses. A particularly preferred synthesis is the following general reaction scheme:

Scheme 1

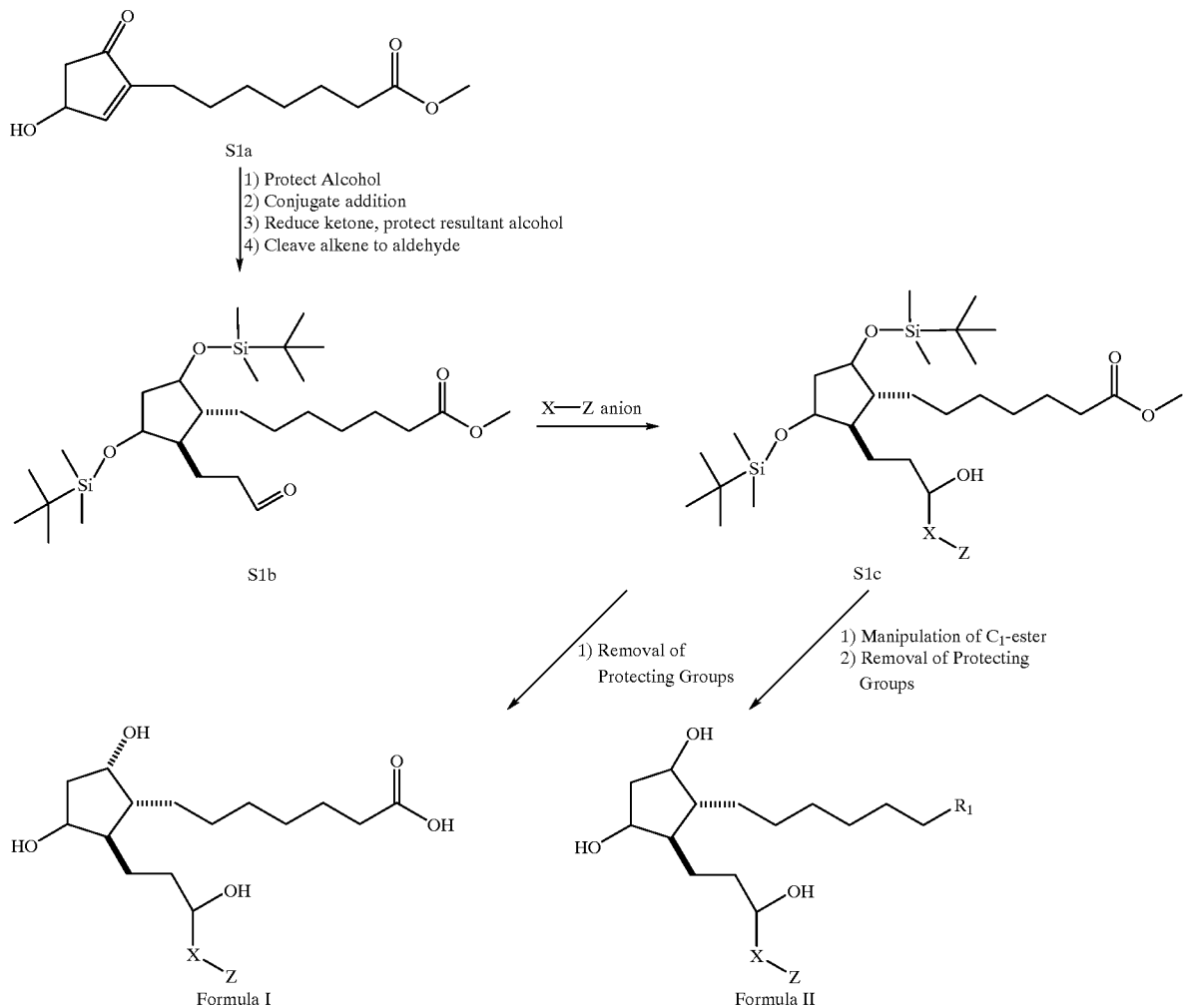

In Scheme 1, $R_1$, $R_2$, X, and Z are as defined above. The methyl 7[3-(R)-hydroxy-5-oxo-1-cyclopent-1-yl] heptanoate (S1a) depicted as starting material for Scheme 1 is commercially available (such as from Sumitomo Chemical or Cayman Chemical).

The $C_{11}$ alcohol of methyl 7-[3-(R)-hydroxy-5-oxo-1-cyclopent-1-yl] protecting group is a silyl group. In the above Scheme 1, methyl 7-[3-(R)-hydroxy-5-oxo-1-cyclopent-1-yl] heptanoate (S1a) is reacted with a silylating agent and base in a solvent that will allow the silylation to proceed. Preferred silylating agents include tert-butyldimethylsilyl chloride and tert-butyldimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halocarbon solvents with dichloromethane being the most preferred solvent. The reaction is allowed to proceed at a temperature preferably between −100° C. and 100° C., more preferably between −80° C. and 80° C., and most preferably between −70° C. and 23° C.

The resulting silylated compound is isolated by methods known to those of ordinary skill in the art. Such methods include, but are not limited to, extraction, solvent evaporation, distillation, and crystallization. Preferably, the silyl ether is purified after isolation by distillation under vacuum.

The silylated compound is then reacted with the cuprate generated via Grignard formation of the appropriate alkenyl bromide as disclosed, for example, in the following references: H. O. House et. al., "The Chemistry of Carbanions: A Convenient Precursor for the Generation of Lithium Organocuprates", *J. Org. Chem.* Vol. 40 (1975) pp. 1460–69; and P. Knochel et. al., "Zinc and Copper Carbenoids as Efficient and Selective a'/d' Multicoupling Reagents", *J. Amer. Chem. Soc.* Vol. 111 (1989) p. 6474–76. Preferred alkenyl bromides include 4-bromo-1-butene, 4-bromo-1-butyne, 4-bromo-2-methyl-1-butene, and 4-bromo-2-ethyl-1-butene. The most preferred alkenyl bromide is 4-bromo-1-butene. Preferred solvents include ethereal solvents, of which diethyl ether and tetrahydrofuran are preferred. The most preferred solvent is tetrahydrofuaran. The Grignard reagent is allowed to form at a temperature between 100° C. and 23° C., more preferably between 85° C. and 30° C., and most preferably between 75° C. and 65° C. The reaction time is preferably between 1 hour and 6 hours, with a more preferred reaction time being between 2 hours and 5 hours, and the most preferred reaction time being between 3 hours and 4 hours.

Once the Grignard reagent is formed, the cuprate is generated from the alkenyl magnesium species. The temperature range for cuprate formation is between −100° C. and 0° C. The preferred temperature range is between −80° C. and −20° C. The more preferred temperature range is between −75° C. and −50° C. The preferred reaction time is between 30 minutes and 6 hours. The more preferred reaction time is between 45 minutes and 3 hours. The most preferred reaction time is between 1 hours and 1.5 hours.

The alkene thus formed is isolated by methods known to one of ordinary skill in the art. Such methods include, but are not limited to, extraction, solvent evaporation, distillation, and crystallization. Preferably, the alkene is purified by flash chromatography on silica gel (Merck, 230–400 mesh) using 10% EtOAc/hexanes as the eluent. The alkene is then reacted with a hydride reducing agent and a polar, protic solvent to give the C-9 alcohol. Preferred reducing agents include lithium aluminum hydride, sodium borohydride, and L-selectride. More preferred reducing agents include sodium borohydride, and L-selectride. The most preferred reducing agent is sodium borohydride. Preferred solvents include methanol, ethanol, and butanol. The most preferred solvent is methanol. The reduction is carried out at a temperature between −100° C. and 23° C. The preferred temperature range is between −60° C. and 0° C. The most preferred temperature range is between −45° C. and −20° C.

The resulting alcohol is isolated by methods known to one of ordinary skill in the art. Such methods include, but are not limited to, extraction, solvent evaporation, distillation, and crystallization. Preferably, the alcohol is purified by flash chromatography on silica gel (Merck, 230–400 mesh) using 20% EtOAc/hexanes as the eluent.

The resultant alcohol can be protected as described previously herein. Preferred silylating agents in this case also include tert-butyldimethylsilyl chloride and tert-butyldimethylsilyl trifluoromethanesulphonate. The most preferred silylating agent is tert-butyldimethylsilyl trifluoromethanesulphonate. Preferred bases include triethylamine, trimethylamine, and 2,6-lutidine. More preferred bases include triethylamine and 2,6-lutidine. The most preferred base is 2,6-lutidine. Preferred solvents include halocarbon solvents with dichloromethane being the most preferred solvent. The reaction is allowed to proceed at a temperature preferably between −100° C. and 100° C., more preferably between −80° C. and 80° C., and most preferably between −70° C. and 23° C.

The resulting silylated compound is isolated by methods known to those of ordinary skill in the art. Such methods include, but are not limited to, extraction, solvent evaporation, distillation, and crystallization. Preferably, the silyl ether is purified after isolation by distillation under vacuum.

The protected or alcohol is then treated with a form of osmium, and sodium periodate in a solvent where they are both soluble. Preferred forms of osmium include osmium tetraoxide and potassium osmate. Preferred solvent systems include 1:1 mixtures of acetic acid and water and 1:1:2 mixtures of water, acetic acid and THF. The result of this treatment is the aldehyde, S1b.

The compound S1b is isolated by methods known to one of ordinary skill in the art. Such methods include, but are not limited to, extraction, solvent evaporation, distillation, and crystallization. Preferably, S1b is purified by flash chromatography on silica gel (Merck, 230–400 mesh) using 20% EtOAc/hexanes as the eluent.

The key intermediate aldehyde depicted as S1b can be reacted with a variety unsaturated carbon nucleophiles to provide the C-9 and C-11-protected 13,14-dihydro-16-tetranor prostaglandin $F_1\alpha$ derivatives depicted as S1c.

With alkyne nucleophiles, the reaction is carried out preferably at between −80° C. and 0° C., more preferably between −80° C. and −20° C., and most preferably between −80° C. and −40° C. Preferred bases for the reaction include n-butyl lithium, s-butyl lithium, t-butyl lithium, and lithium diisopropyl amide (LDA). Preferred solvents for the reaction are ether solvents. Preferred solvents include diethyl ether, and tetrahydrofuran. The most preferred solvent is tetrahydrofuran. With heterocyclic nucleophiles, preferred solvents include ethereal solvents. More preferred ethereal solvents include diethyl ether, dibutyl ether and tetrahydrofuran. The most preferred ethereal solvent is tetrahydrofuran.

The resulting compounds depicted as S1c can then be deprotected using techniques known to one of ordinary skill in the art, and isolated yielding the 13,14-dihydro-15-substituted-15-pentanor prostaglandin F1ot derivatives depicted by Formula I. Compounds depicted by Formula I are exemplified in Examples 1–43.

Compounds depicted by Formula II can be made directly from the C-9 and C-11-protected 13,14-dihydro-16-tetranor prostaglandin $F_1\alpha$ derivatives depicted as S1c by methods known to one of ordinary skill in the art. For example, the condensation of methyl esters of S1c with amines or hydroxylamine provides compounds depicted by Formula II. Compounds depicted by Formula II are exemplified in Examples 44–47. These compounds are isolated by methods known to one of ordinary skill in the art. Such methods include, but are not limited to, extraction, solvent evaporation, distillation, and crystallization.

The following non-limiting examples illustrate the compounds, compositions, and uses of the present invention.

EXAMPLES

Compounds are analyzed using $^1$H and $^{13}$C NMR, Elemental analysis, mass spectra, high resolution mass spectra and/or IR spectra as appropriate.

Typically, inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis is performed on glass mounted silica gel plates (200–300 mesh; J. T. Baker) and visualized using uv light, 5% phosphomolybdic acid in EtOH, or ammonium molybdate/cerric sulfate in 10% aqueous $H_2SO_4$.

Example 1

Preparation of 13,14-dihydro-15-(thianaphthyl) pentanor prostaglandin $F_1\alpha$

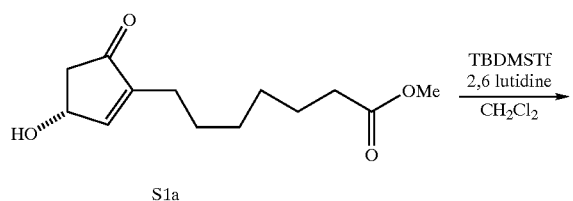

S1a

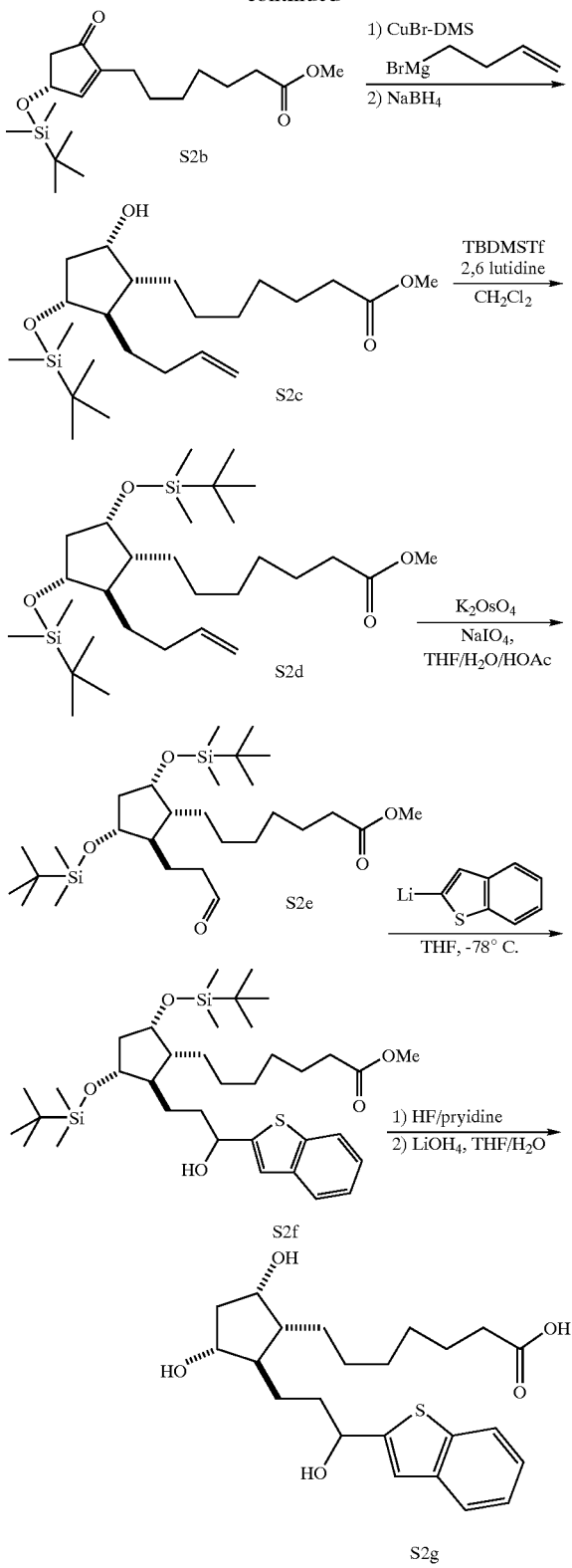

a. Methyl 7-(2-oxo-4-(1,1,2,2-tetramethyl-1-silapropoxy)cyclopent-1-enyl) heptanoate S2b To a solution of Methyl-7-[3-(R)-hydroxy-5-oxo-1-cyclopenten-1-yl] heptanoate S2a (1 equiv.) in CH$_2$Cl$_2$ at −78° C. is added 2,6 Lutidine (1.3 equiv.) dropwise over 15 minutes. The solution is kept at −78° C., and TBDMS Triflate (1.2 equiv.) in CH$_2$Cl$_2$ is added dropwise over 15 minutes. The reaction is warmed gradually to room temperature and stirred at room temperature for 15 hours. Aqueous 10% HCl is added and the layers are separated. The water layer is extracted with CH$_2$Cl$_2$ and the organic layers are combined. The organic layer is washed with brine, dried (Na$_2$SO$_4$) and concentrated. The residue is distilled under vacuum (10 mm Hg) to provide the silyl ether S2b.

b. Methyl 7-(5-but-3-enyl-2-hydroxy-4-(1,1,2,2-tetramethyl-1-silapropoxy)cyclopentyl) heptanoate S2c To a slurry of Mg° powder (2 equiv.) in THF at room temperature is added one crystal of iodine (catalytic 1$_2$)and 1-bromobutene (2 equiv.) dropwise over 10 minutes. The reaction proceeds to exotherm as the addition continues. After the addition is complete, the reaction is refluxed for 3 hours and cooled to room temperature. The Grignard is diluted with THF and added via cannula to a 3-necked flask equipped with mechanical stirring and charged with CuBr.DMS (2 equiv.) in a 1:1 solution of THF/DMS at −78° C. After the addition of the Grignard (20 min), the reaction is stirred for 1 hour at −78° C. The color of the reaction is dark red at this point. A solution of the ketone S2b (1 equiv.) in THF is then added dropwise over 25 minutes. The reaction is stirred at −78° C. for 15 minutes, then allowed to warm slowly to room temperature over 2 hours. The reaction is quenched with aqueous NH$_4$Cl and the excess DMS is allowed to evaporate overnight. The reaction is partitioned between brine/CH$_2$Cl$_2$and the layers are separated. The aqueous layer is back-extracted with CH$_2$Cl$_2$ and the organic layers are combined and dried (Na$_2$SO$_4$). The solvent is removed in vacuo and the residue is chromatographed on SiO$_2$ (10% hexane/EtOAc) to give the ketone precursor to S2c.

The ketone precursor to S2c (1 equiv.) is dissolved in MeOH and cooled to −40° C. Sodium borohydride (0.9 equiv.) is added portionwise over 10 minutes. After the addition is complete, the reaction is stirred for 13 hours at −40° C. and then for 12 hours at −78° C. The reaction is quenched with water, partitioned between brine and CH$_2$Cl$_2$, and the layers separated. The aqueous layer is back-extracted with CH$_2$Cl$_2$ and the organic layers are combined and dried (Na$_2$SO$_4$). The solvent is removed in vacuo and the residue chromatographed on SiO$_2$ (30% EtOAc/hexanes) to give the alcohol S2c.

c. Methyl 7-(5-but-3-enyl-2,4-di(1,1,2,2-tetramethyl-1-silapropoxy) cyclopentyl) heptanoate S2d The alcohol S2c (1 equiv.) is dissolved in CH$_2$Cl$_2$ and cooled to 0° C. and added is 2,6 lutidine (1.3 equiv.) dropwise over 15 minutes. The solution is kept at −78° C., and TBDMS Triflate (1.2 equiv.) in CH$_2$Cl$_2$ is added dropwise over 15 minutes. The reaction is warmed gradually to room temperature and stirred at room temperature for 15 hours. Aqueous 10% HCl is added and the layers are separated. The water layer is extracted with CH$_2$Cl$_2$ and the organic layers are combined. The organic layer is washed with brine, dried (Na$_2$SO$_4$) and concentrated. The residue is chromatographed (10% EtOAc in hexanes) to provide the silyl ether S2d.

d. Methyl 7-(5-(3-oxopropanyl)-2,4-di(1,1,2,2-tetramethyl-1-silapropoxy) cyclopentyl) heptanoate S2e In a 50 mL round-bottomed flask, Sodium periodate (2 equiv.) and 10 mL of water are added. This is stirred until the periodate has completely dissolved. Then an equal portion of glacial acetic acid is added, followed by two portions of tetrahydrofuran. Finally, a few mole percent of potassium osmate are added, followed by the alkene S2d (1 equiv.). The reaction is stirred at room temperature under nitrogen with TLC being used to monitor the reaction. When no starting material is evident by TLC, The reaction is quenched with brine and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) S2e is obtained.

e. Methyl 7-(5-(3-hydroxy-3-thianaphthyl-propanyl)-2,4-di(1,1,2,2-tetramethyl-1-silapropoxy) cyclopentyl) heptanoate S2f The aldehyde S2e is dissolved in a few mL of dry THF and is added dropwise to a −78° C. THF solution of the lithium anion of thianapthylene (prepared by combining n-butyl lithium and thianaphthylene at −78° C.) a 50 mL round-bottomed flask. This is stirred until the reaction has ceased to progress as evidenced by TLC. Then the reaction is quenched at −78° C. with a saturated solution of ammonium chloride and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) S2f is obtained.

f. 13,14-dihydro-15-(thianaphthyl)-15-pentanor prostaglandin $F_{1a}$ (S2g)

To a small round-bottomed flask, is added methyl ester S2f and 3 mL of $CH_3CN$ and 0.1 mL of HF/Pyridine (0.1 mmol, 1 equiv.) are added while the flask is warmed from 0° C. to room temperature. After 3 hours at 21° C., the reaction is quenched with saturated aqueous NaCl. The aqueous layer is extracted three times with $CH_2Cl_2$. The organic layers are combined and washed three time with 1N HCl, brine, and dried ($Na_2SO_4$). After column chromatography, (7:3, Hexane: Ethyl Acetate) a clear oil is obtained. This oil is added to a few mL of a 3:1 THF: water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3 times with methylene chloride, the organic layers are combined and washed with brine, dried ($Na_2SO_4$), concentrated in vacuo, and the residue is chromatographed (methylene chloride, methanol, acetic acid, 9.6, 0.4, 0.015), to provide S2g.

Examples 2–22

Examples 2–22 are prepared using substantially the same procedures as those described in Example 1, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 2

13,14-dihydro-15-(2-benzathiozoly)-15-pentanor Prostaglandin $F_1\alpha$

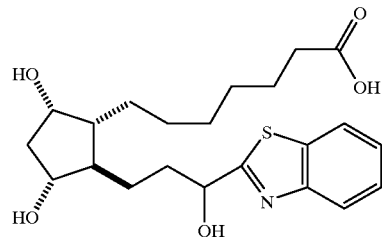

Example 3

13,14-dihydro-15-(7-fluorobenzathiozoly)-15-pentanor Prostaglandin $F_1\alpha$

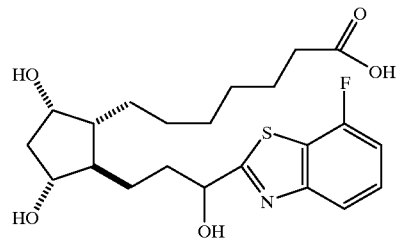

Example 4

13,14-dihydro-16-ynyl-17-(2,5-difluorophenyl)-17-trinor Prostaglandin $F_1\alpha$

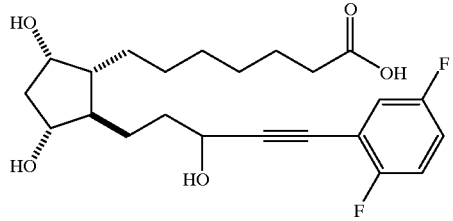

Example 5

13,14-dihydro-16-ynyl-17-(2,3-difluorophenyl)-17-trinor Prostaglandin $F_1\alpha$

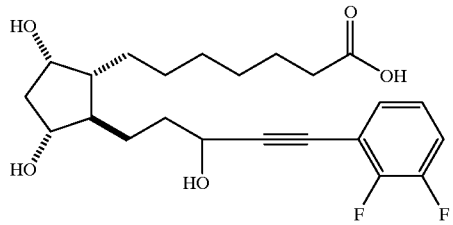

Example 6

13,14-dihydro-16-ynyl-17-(3,5-difluorophenyl)-17-trinor Prostaglandin $F_1\alpha$

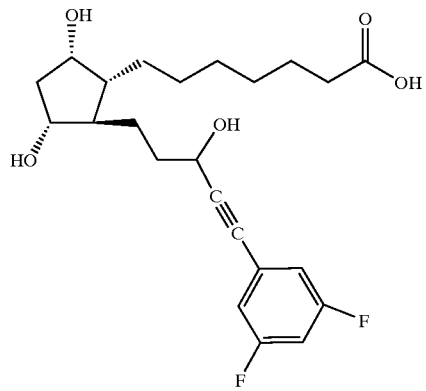

Example 7

13,14-dihydro-16-ynyl-17-(3,4-difluorophenyl)-17-trinor Prostaglandin $F_1\alpha$

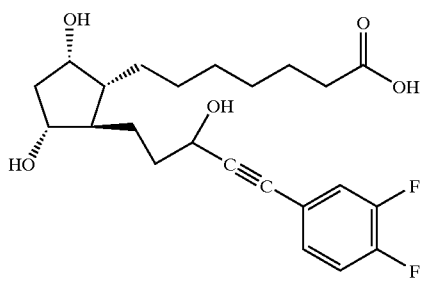

Example 8

13,14-dihydro-15-(6-fluorothianapthyl)-15-pentanor Prostaglandin $F_1\alpha$

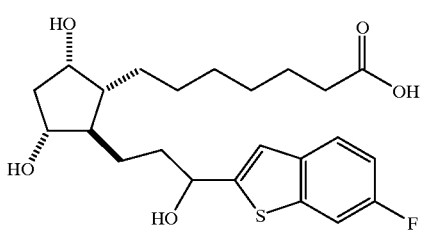

Example 9

13,14-dihydro-15-(6-ynyl-17-(2,4-difluorophenyl) 17trinor Prostaglandin $F_1\alpha$

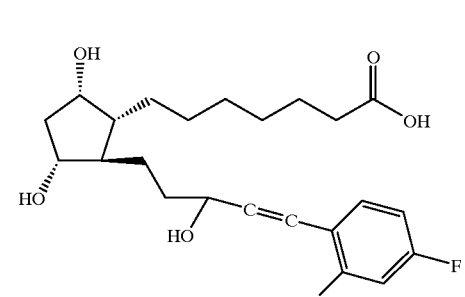

Example 10

13,14-dihydro-16-ynyl-17-(3-fluorophenyl)-17-trinor Prostaglandin F1αmethyl ester

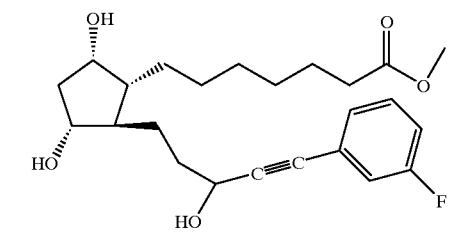

Example 11

13,14-dihydro-16-ynyl-17-(2-fluoro-4-methylphenyl)-17-trinor Prostaglandin F1α

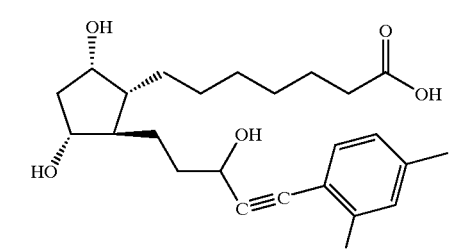

Example 12

13,14-dihydro-16-ynyl-17-(4-chlorophenyl)-17-trinor Prostaglandin F1α

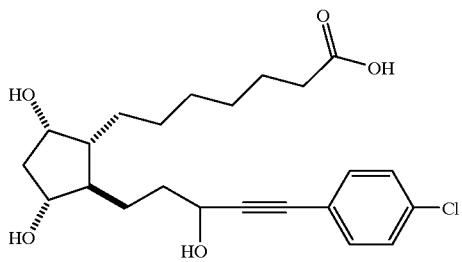

Example 13

13,14-dihydro-16-ynyl-17-phenyl-17-trinor Prostaglandin F1α isopropyl ester

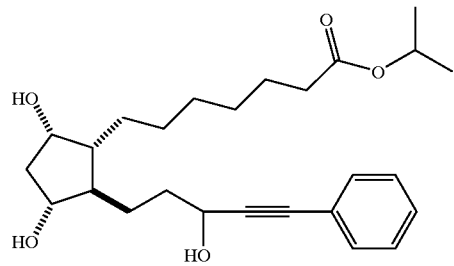

Example 14

13,14-dihydro-16-ynyl-17-(4-fluorophenyl)-17-trinor Prostaglandin F1α ethyl ester

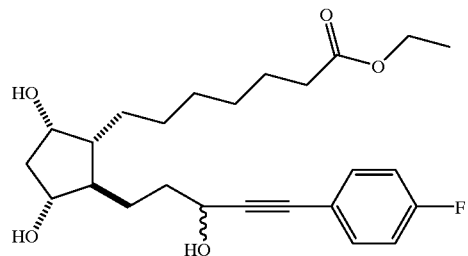

Example 15

13,14-dihydro-15-(5-fluorobenzothiazolyl)-15-pentanor Prostaglandin F1α isopropyl ester

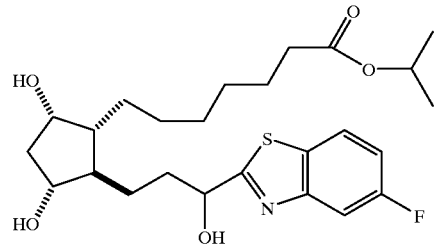

Example 16

13,14-dihydro-16-ynyl-17-(2-chlorophenyl)-17-trinor Prostaglandin F1α

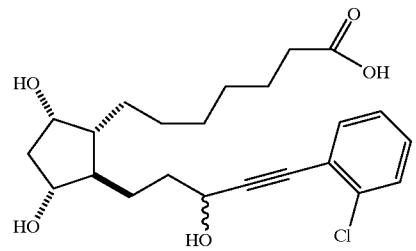

Example 17

13,14-dihydro-16-ynyl-17-(2-fluorophenyl)-17-trinor Prostaglandin F1α methyl ester

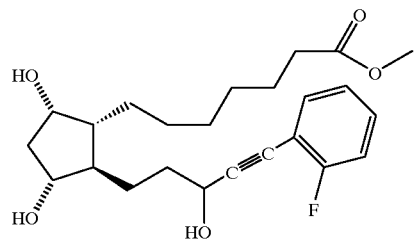

Example 18

13,14-dihydro-16-ynyl-17-(2-fluorophenyl)-17-trinor Prostaglandin F1α

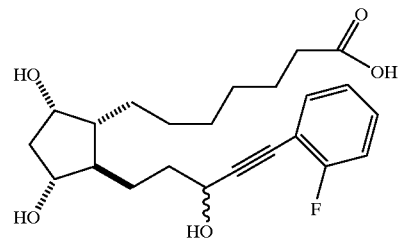

Example 19

13,14-dihydro-16-ynyl-17-(4-phenylphenyl)-17-trinor Prostaglandin F1α

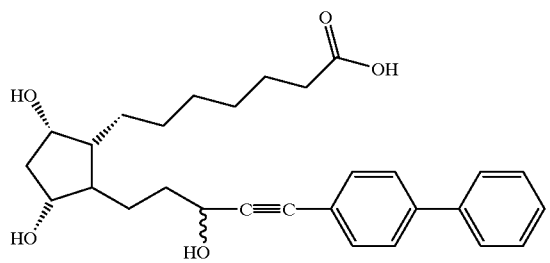

Example 20

13,14-dihydro-16-ynyl-18-phenyl-18-dinor Prostaglandin F1α

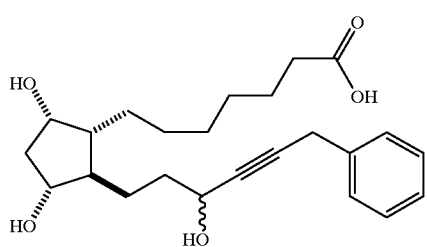

Example 21

13,14-dihydro-16-ynyl-17-(4-methylphenyl)-17-trinor Prostaglandin F1α

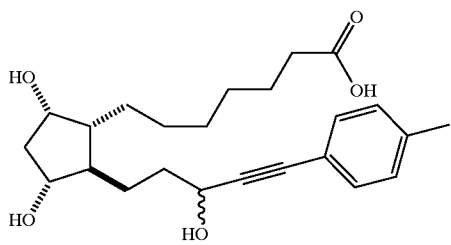

Example 22

13,14-dihydro-16-ynyl-18-(2-fluorophenyl)-18-dinor Prostaglandin F1α

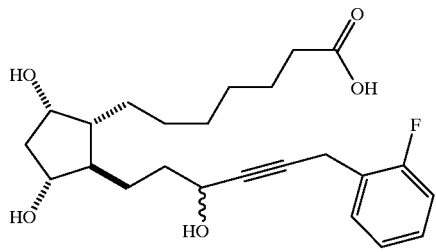

Example 23

Preparation of 13,14-dihydro-15-phenyl-15-pentanor prostaglandin F1α

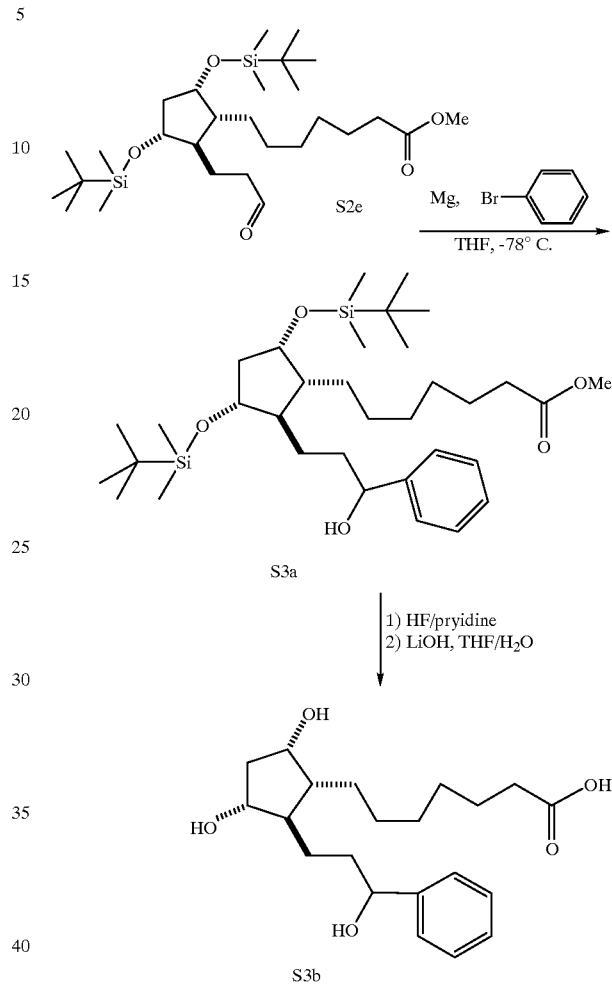

a. Methyl 7-(5-(3-hydroxy,3-phenyl-propanyl)-2,4-di(1,1,2,2-tetramethyl-1-silapropoxy) cyclopentyl) heptanoate S3a The aldehyde S2e from Example 1 is dissolved in a few mL of dry THF and is added dropwise to a −78° C. THF solution of the Grignard species (prepared by combining Magnesium and bromobenzene at 0° C.) a 50 mL round-bottomed flask. This is stirred until the reaction has ceased to progress as evidenced by TLC. Then the reaction is quenched at −78° C. with a saturated solution of ammonium chloride and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) S3a is obtained.

b. 13,14-dihydro-15-phenyl-15-pentanor prostaglandin F. (S3b)

To a small round-bottomed flask, is added methyl ester S3a and 3 mL of CH₃CN and 0.1 mL of HF/Pyridine (0.1 mmol, 1 equiv.) are added while the flask is warmed from 0° C. to room temperature. After 3 hours at 21° C., the reaction is quenched with saturated aqueous NaCl. The aqueous layer is extracted three times with $CH_2Cl_2$. The organic layers are combined and washed three time with 1N HCl, brine, and dried ($Na_2SO_4$). After column chromatography, (97:3, dichloromethane:methanol) a clear oil is obtained. This oil is added to a few mL of a 3:1 THF: water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3 times with methylene chloride, the organic layers are combined and washed with brine, dried ($Na_2SO_4$), concentrated in vacuo, and the residue is chromatographed (methylene chloride, methanol, acetic acid, 9.6, 0.4, 0.015), to provide S3b.

Examples 24–35

Examples 24–35 are prepared using substantially the same procedures as those described in Example 23, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 24

13,14-dihydro-15-(4-methylphenyl)-15-pentanor Prostaglandin $F_1\alpha$

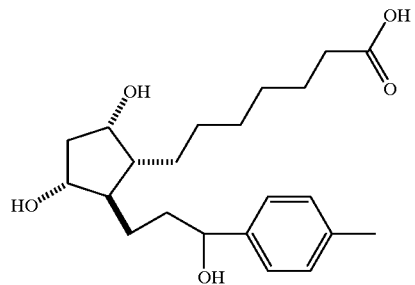

Example 25

13,14-dihydro-15-(4-trifluoromethylphenyl)-15-pentanor Prostaglandin $F_1\alpha$

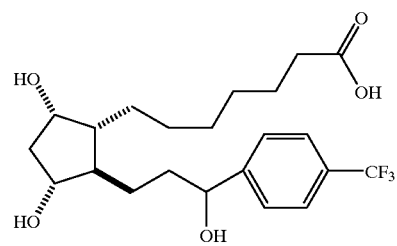

Example 26

13,14-dihydro-15 (3-trifluoromethylphenyl)-15-pentanor Prostaglandin $F_1\alpha$

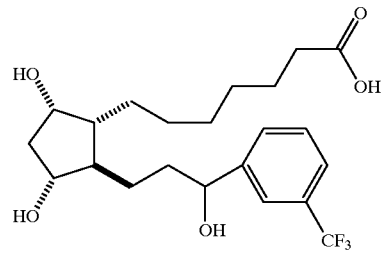

Example 27

13,14-dihydro-15-(2-fluorophenyl)-15-pentanor Prostaglandin $F_1\alpha$

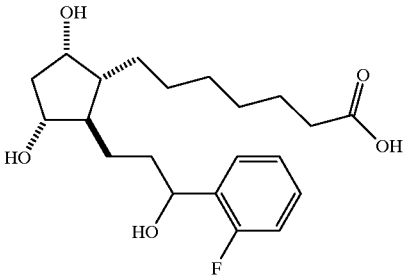

Example 28

13,14-dihydro-15-(3,5 difluorophenyl)-15-pentanor Prostaglandin $F_1\alpha$ ethyl ester

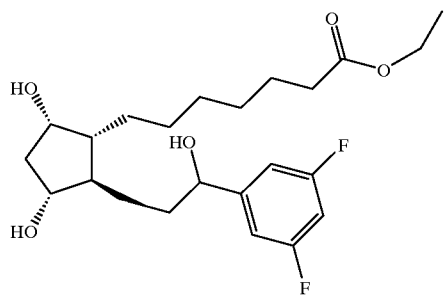

Example 29

13,14-dihydro-15-(3-chloro-4-fluoro-6-methylphenyl)-15-pentanor Prostaglandin $F_1\alpha$

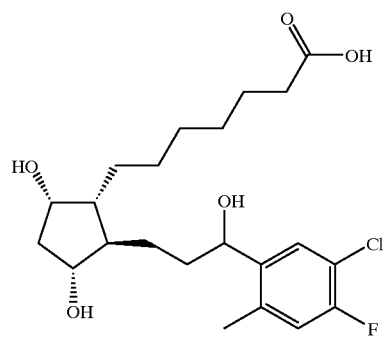

Example 30

13,14-dihydro-15 (3-pyridinyl)-15-pentanor Prostaglandin $F_1\alpha$

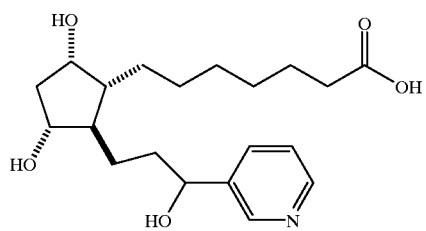

Example 31

13,14-dihydro-15 (2-chlorophenyl)-15-pentanor Prostaglandin $F_1\alpha$

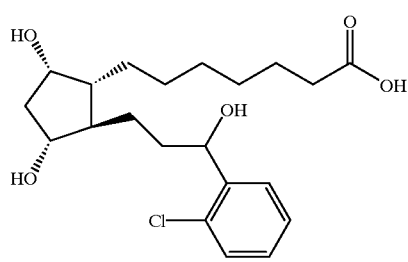

Example 32

13,14-dihydro-15 (4-phenylphenyl)-15-pentanor Prostaglandin $F_1\alpha$

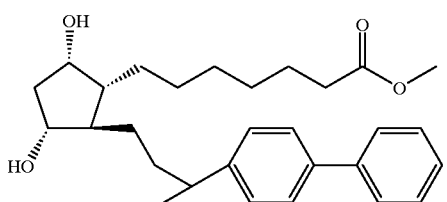

Example 33

13,14-dihydro-15-S-(2-fluorophenyl)-15-pentanor Prostaglandin $F_1\alpha$

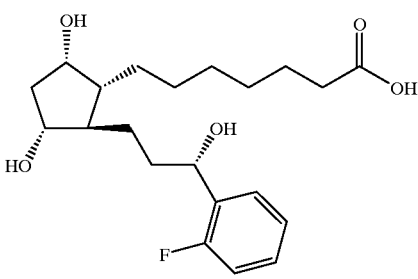

Example 34

13,14-dihydro-15-S-(2-fluoronaphthyl)-15-pentanor Prostaglandin $F_1\alpha$

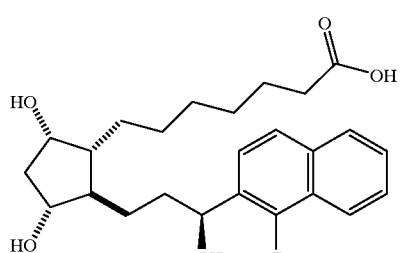

Example 35

13,14-dihydro-15 (2-fluoro-4-pyridyl)-15-pentanor Prostaglandin F₁α isopropyl ester

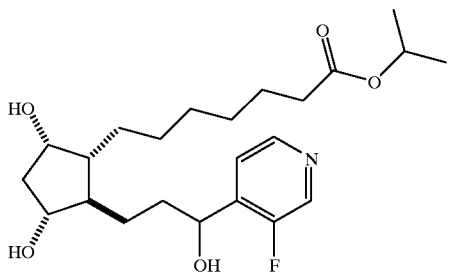

Example 36

Preparation of 13,14-dihydro-15-(6-methylnaphth-2-yl)-15-pentanor prostaglandin F₁α:

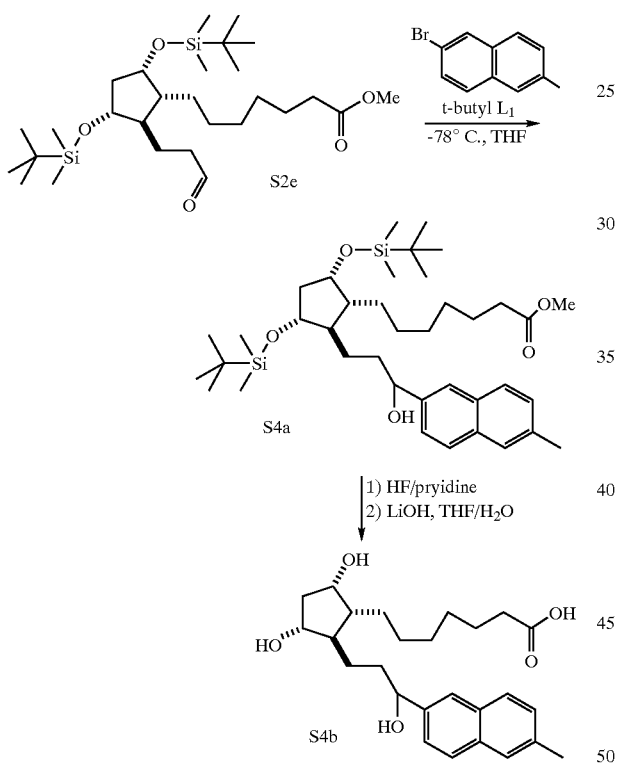

a. Methyl 7-(5-(3-hydroxy,(4-methyl-2-napththyl)-propanyl)-2,4-di(1,1,2,2-tetramethyl-1-silapropoxy)cyclopentyl) heptanoate S4a The aldehyde S2e from Example 1 is dissolved in a few mL of dry THF and is added dropwise to a −78° C. THF solution of naphthyl anion (prepared by t-butyl Lithium and the naphthyl bromide at −78° C.) a 50 mL round-bottomed flask. This is stirred until the reaction has ceased to progress as evidenced by TLC. Then the reaction is quenched at −78° C. with a saturated solution of ammonium chloride and is extracted with ethyl acetate and hexanes in a 4:1 ratio. The organic layer is washed with brine to neutral pH, dried over sodium sulfate, and concentrated. After column chromatography, (7:3, Hexane: Ethyl Acetate) S4a is obtained.

b. 13,14-dihydro-16,17-dehydro-15-(6-methyl-2-naphthyl)-15-pentanor prostaglandin F₁ (S4b)

To a small round-bottomed flask, is added methyl ester S4a and 3 mL of CH₃CN and 0.1 mL of HF/Pyridine (0.1 mmol, 1 equiv.) are added while the flask is warmed from 0° C. to room temperature. After 3 hours at 21° C., the reaction is quenched with saturated aqueous NaCl. The aqueous layer is extracted three times with CH₂Cl₂. The organic layers are combined and washed three time with 1N HCl, brine, and dried (Na₂SO₄). After column chromatography, (97:3, dichlormethane:methanol) a clear oil is obtained. This oil is added to a few mL of a 3:1 THF: water solution, and the flask is cooled to 0° C. An excess amount (2.5 equiv.) of lithium hydroxide is added, the ice bath is removed, and the reaction is stirred at room temperature overnight. Methylene chloride and saturated citric acid are added to the reaction mixture, the aqueous layer is washed 3 times with methylene chloride, the organic layers are combined and washed with brine, dried (Na₂SO₄), concentrated in vacuo, and the residue is chromatographed (methylene chloride, methanol, acetic acid, 9.6, 0.4, 0.015), to provide S4b.

Examples 37–42

Examples 37–42 are prepared using substantially the same procedures as those described in Example 36, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 37

13,14-dihydro-15-(benzo[b]thiophen-5-yl)-15-pentanor prostaglandin F₁

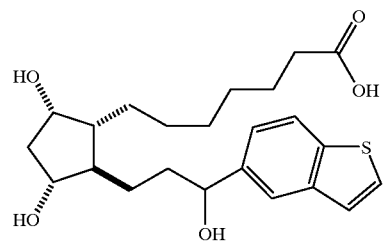

Example 38

13,14-dihydro-15-(6-benzothiazol-5-yl)-15-pentanor prostaglandin F₁

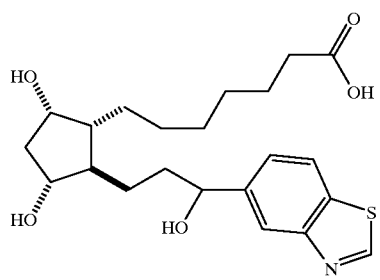

Example 39

13,14-dihydro-15-(benzo[b]furan-5-yl)-15-pentanor prostaglandin $F_1$ methyl ester

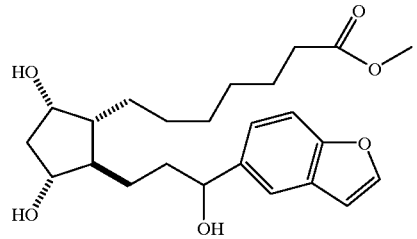

Example 40

13,14-dihydro-15-(5-fluoronaphthyl)-15-pentanor prostaglandin $F_1$

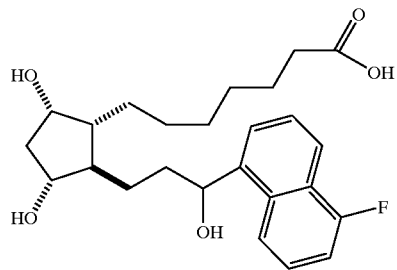

Example 41

13,14-dihydro-15-(8-fluoro-2-naphthyl)-15-pentanor prostaglandin $F_1$.

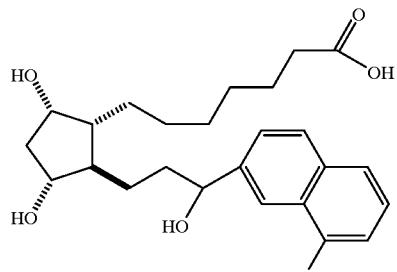

Example 42

13,14-dihydro-15-(S-trifluoromethyl-2-naphthyl)-15-pentanor prostaglandin $F_1$

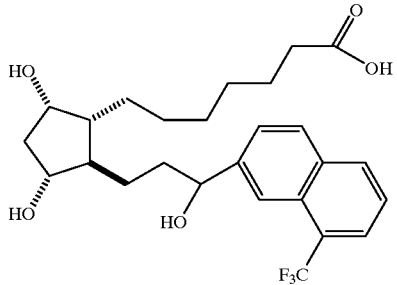

Example 43

13,14-dihydro-15-(1-fluoro-3-trifluoromethyl-2-naphthyl)-15-pentanor prostaglandin $F_1$ isopropyl ester

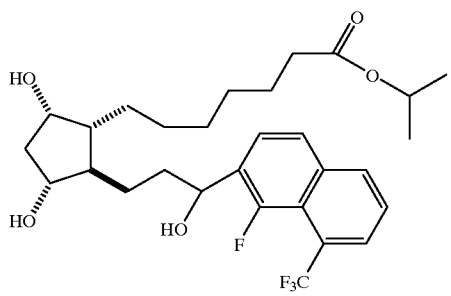

Example 44

Preparation of 13,14-dihydro-16-ynyl-17-(2-fluorophenyl)-17-trinor Prostaglandin F1α 1-hydroxamic acid:

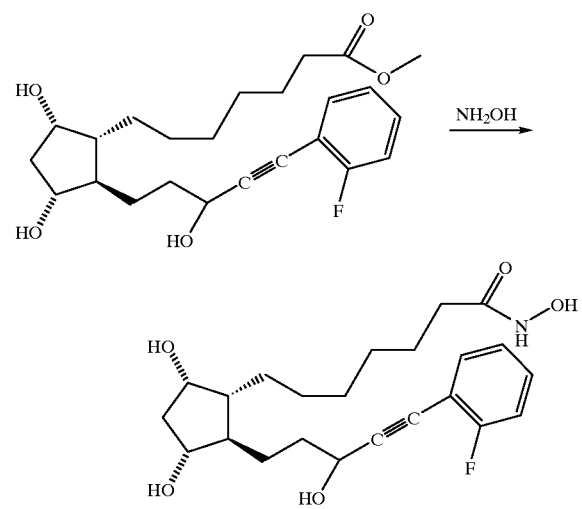

In a flame-dried 25 mL round-bottomed flask equipped with a magnetic stir bar is placed 13,14-dihydro-16,17-didehydro-17-o-fluorophenyl trinor Prostaglandin F1α methyl ester (Example 17) (1.0 equiv.) in methanol. To this solution is added hydroxylamine in methanol (1.25 equiv.). The solution stirred for a few minutes. The solution is then treated with 1N hydrochloric acid and extracted with ethyl acetate. The organic layer is washed with brine, dried over anhydrous MgSO$_4$, filtered and concentrated under reduced pressure. The residue is purified by chromatography to give 13,14-dihydro-16,17-didehydro-17-o-fluorophenyl trinor Prostaglandin F1α 1-hydroxamic acid.

Examples 45–47

Examples 45–47 are prepared using substantially the same procedures as those described in Example 44, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 45

13,14-dihydro-15-(benzathiozolyl)-15-pentanor Prostaglandin F$_1$α 1-hydroxamic acid

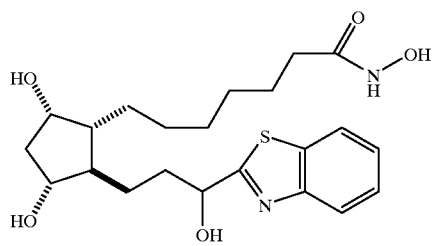

Example 46

13,14-dihydro-15-(5-fluorothianaphthyl)-15-pentanor Prostaglandin F$_1$α 1-hydroxamic acid

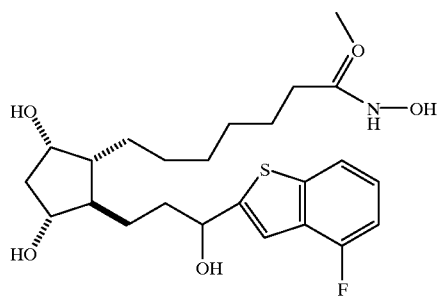

Example 47

13,14-dihydro-15thianaphthyl-15-pentanor Prostaglandin F$_1$α 1-N-methanesulfonamide

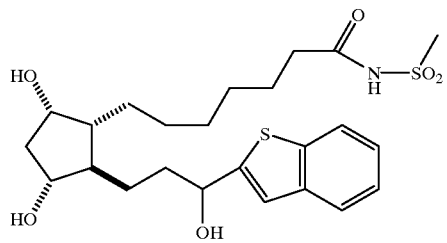

Compositions

Compositions of the subject invention comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

In addition to the compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a subject. The term "compatible", as used herein, means that the components of the composition are capable of being commingled with the compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the subject being treated.

Some examples of substances which can serve as pharmaceutically-acceptable carriers or components thereof are sugars, such as lactose, glucose and sucrose; starches, such as cornstarch and potato starch; cellulose and its derivatives, such as sodium carboxymethyl cellulose, ethyl cellulose, cellulose acetate; powdered tragacanth; malt; gelatin; talc; solid lubricants, such as stearic acid, magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; alginic acid; emulsifiers, such as the Tweens®; wetting agents such as sodium lauryl sulfate; coloring agents; flavoring agents, excipients; tableting agents; stabilizers; antioxidants; preservatives; pyrogen-free water; isotonic saline; and phosphate buffer solutions.

The choice of a pharmaceutically-acceptable carrier to be used in conjunction with a compound is basically determined by the way the compound is to be administered. The compounds of the present invention may be administered systemically. Routes of administration include transdermal; oral; parenterally, including subcutaneous or intravenous injection; topical; and/or intranasal.

The appropriate amount of the compound to be used may be determined by routine experimentation with animal models. Such models include, but are not limited to the intact and ovariectomized rat models, the ferret, canine, and non human primate models as well as disuse models.

Preferred unit dosage forms for injection include sterile solutions of water, physiological saline, or mixtures thereof. The pH of said solutions should be adjusted to about 7.4. Suitable carriers for injection or surgical implants include hydrogels, controlled- or sustained release devises, polylactic acid, and collagen matrices.

Suitable pharmaceutically-acceptable carriers for topical application include those suited for use in lotions, creams, gels and the like. If the compound is to be administered perorally, the preferred unit dosage form is tablets, capsules and the like. The pharmaceutically-acceptable carriers suitable for the preparation of unit dosage forms for oral administration are well-known in the art. Their selection will depend on secondary considerations like taste, cost, and shelf stability, which are not critical for the purposes of the subject invention, and can be made without difficulty by those skilled in the art.

Methods of Use

The compounds of the present invention are useful in treating many medical disorders, including for example, ocular disorders, hypertension, fertility control, nasal congestion, neurogenic bladder disorder, gastrointestinal disorders, dermatological disorders, and osteoporosis.

The compounds of the present invention are useful in increasing bone volume and trabecular number through formation of new trabeculae, bone mass while maintaining a normalized bone turnover rate, and formation at the endosteal surface without removing bone from the existing cortex. Thus, these compounds are useful in the treatment and prevention of bone disorders.

The preferred routes of administration for treating bone disorders are transdermal and intranasal. Other preferred routes of administration include rectal, sublingual, and oral.

The dosage range of the compound for systemic administration is from about 0.01 to about 1000 µg/kg body weight, preferably from about 0.1 to about 100 µg/kg per body weight, most preferably form about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

Composition and Method Examples

The following non-limiting examples illustrate the subject invention. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

Pharmaceutical compositions in the form of tablets are prepared by conventional methods, such as mixing and direct compaction, formulated as follows:

| Ingredient | Quantity (mg per tablet) |
|---|---|
| Compound of Example 1 | 5 |
| Microcrystalline Cellulose | 100 |
| Sodium Starch Glycollate | 30 |
| Magnesium Stearate | 3 |

When administered orally once daily, the above composition substantially increases bone volume in a patient suffering from osteoporosis.

Example B

Pharmaceutical compositions in liquid form are prepared by conventional methods, formulated as follows:

| Ingredient | Quantity |
|---|---|
| Compound of Example 32 | 1 mg |
| Phosphate buffered physiological saline | 10 ml |
| Methyl Paraben | 0.05 ml |

When 1.0 ml of the above composition is administered subcutaneously once daily, the above composition substantially increases bone volume in a patient suffering from osteoporosis.

Example C

Topical pharmaceutical compositions for lowering intraocular pressure are prepared by conventional methods and formulated as follows:

| Ingredient | Amount (wt %) |
|---|---|
| Compound of Example 1 | 0.004 |
| Dextran 70 | 0.1 |
| Hydroxypropyl methylcellulose | 0.3 |
| Sodium Chloride | 0.77 |
| Potassium chloride | 0.12 |
| Disodium EDTA (Edetate disodium) | 0.05 |
| Benzalkonium chloride | 0.01 |
| HCL and/or NaOH | pH 7.2–7.5 |
| Purified water | q.s. to 100% |

While particular embodiments of the subject invention have been described, it would be obvious to those skilled in the art that various changes and modifications to the compositions disclosed herein can be made without departing from the spirit and scope of the invention. It is intended to cover, in the appended claims, all such modifications that are within the scope of this invention.

What is claimed is:

1. A compound having the structure:

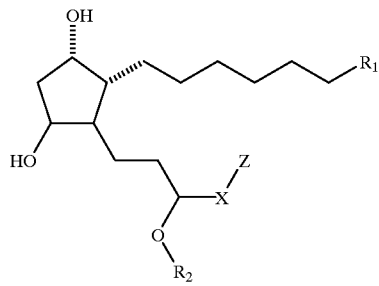

wherein
a) $R_1$ is selected from the group consisting of $CO_2H$, $C(O)NHOH$, $C_2R_3$, $CH_2OH$, $S(O)_2R_3$, $C(O)NHR_3$, $C(O)NHS(O)_2R_4$, and tetrazole, wherein $R_3$ is alkyl, heteroalkyl, carbocyclic aliphatic ring, heterocyclic alphatic ring, monocyclic aromatic ring, or monocyclic heteroaromatic ring; and
$R_4$ is alkyl, heteroalkyl, carbocyclic aliphatic ring, heterocyclic aliphatic ring, monocyclic aromatic ring, or monocyclic heteroaromatic ring;
(b) $R_2$ is H or lower alkyl;
(c) X is a covalent bond;
(d) Z is an aromatic ring or a heteroaromatic ring provided that when Z is a heteroaromatic ring and X is a covalent bond, Z is attached to $C_{15}$ via a Carbon member atom; and
(e) any optical isomer, diastereomer enantiomer of the above structure or a pharmaceutically-acceptable salt, or bio-hydrolyzable amide, ester, or imide thereof.

2. The compound of claim 1 wherein $R_1$ is selected from the group consisting of $CO_2H$, $C(O)NHOH$, $CO_2R_3$, $C(O))NHS(O)_2R_4$, or tetrazole.

3. The compound of claim 2 wherein Z is a bicyclic heteroaromatic ring.

4. The compound of claim 3 wherein Z is selected from the group consisting of:
benzo[β]thiazolyl, benzo[β]thiophenyl, and benzoxazolyl.

5. The compound of claim 4 wherein Z is substituted with one substituent, said one substitutent being selected from the group consisting of:
lower alkyl halo, and haloalkyl.

6. The compound of claim 4 wherein $R_2$ is H.

7. The compound of claim 6 wherein $R_1$ is $CO_2H$ or $CO_2R_3$.

8. A method of treating a human or other animal subject having a bone disorder, said method comprising administering to said subject a compound according to the structure:

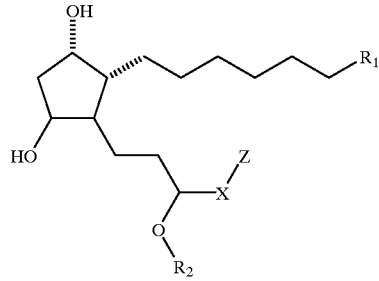

wherein
(a) $R_1$ is selected from the group consisting of $CO_2H$, $C(O)NHOH$, $CO_2R_3$, $CH_2OH$, $S(O)_2R_3$, $C(O)NHR_3$, $C(O)NHS(O)_3R_4$, and tetrazole;

wherein $R_1$ is alkyl, heteroalkyl, carbocyclic aliphatic ring, heterocyclic aliphatic ring, monocyclic aromatic ring, or monocyclic heteroaromatic ring; and
$R_4$ is alkyl, heteroalkyl, carbocyclic aliphatic ring, heterocyclic aliphatic ring, monocyclic aromatic ring, or monocyclic heteroaromatic ring;
(b) $R_3$ is H or lower alkyl;
(c) X is a covalent bond;
(d) Z is an aromatic ring or a heteroaromatic ring provided that when Z is a heteroaromatic ring and X is a covalent bond, Z is attached to $C_{15}$ via a Carbon member atom; and
(e) any optical isomer, diastereomer, enantiomer of the above structure or a pharmaceutically-acceptable salt, or bio-hydrolyzable, amide, ester, or imide thereof.

9. The method of claim 8 wherein said bone disorder is osteoporosis.

10. The method of claim 9 wherein in osteoporosis is post-menopausal.

11. The method of claim 9 wherein in osteoporosis is cortico-steroid induced.

12. The method of claim 8 wherein said bone disorder is osteopenia.

13. The method of claim 8 wherein said bone disorder is a bone fracture.

14. The method of claim 8 wherein said compound is administered orally.

15. The method of claim 8 wherein said compound is administered transdermally.

16. The method of claim 8 wherein said compound is administered intranasally.

17. A method of treating glaucoma, said method comprising administering to human or other animal a safe and effective amount of a compound according to the structure:

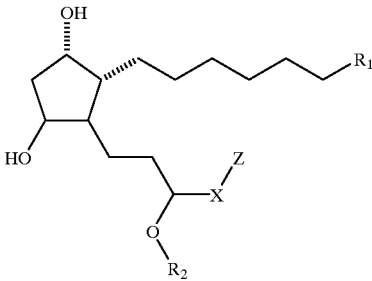

wherein
(a) $R_1$ is selected from the group consisting of $CO_3H$, $C(O)NHOH$, $CO_2R_3$, $CH_2OH$, $S(O)_2R_3$, $C(O)NHR_3$, $C(O)NHS(O)_2R_4$, and tetrazole;
wherein $R_1$ is alkyl, heteroalkyl, carbocyclic aliphatic ring, heterocyclic aliphatic ring, monocyclic aromatic ring, or monocyclic heteroaromatic ring; and
$R_4$ is alkyl, heteroalkyl, carbocyclic aliphatic ring, heterocyclic aliphatic ring, monocyclic aromatic ring, or monocyclic heteroaromatic ring;
(b) $R_2$ is H or lower alkyl;
(c) X is a covalent bond;
(d) Z is an aromatic ring or a heteroaromatic ring provided that when Z is a heteroaromatic ring and X is a covalent bond, Z is attached to $C_{15}$ via a Carbon member atom; and
(e) any optical isomer, diastereomer, enantiomer of the above structure or a pharmaceutically-acceptable salt, or bio-hydrolyzable, amide, ester, or imide thereof.

18. The method of claim 17, wherein said compound is administered topiclally.

* * * * *

UNITED STATES PATENT AND TRADEMARK OFFICE
CERTIFICATE OF CORRECTION

PATENT NO.    : 6,586,463 B2
DATED         : July 1, 2003
INVENTOR(S)   : Mitchell Anthony deLong et al.

It is certified that error appears in the above-identified patent and that said Letters Patent is hereby corrected as shown below:

<u>Column 2,</u>
Line 67, delete "I" and insert -- 1 --.

<u>Column 30,</u>
Line 3, delete "15thianaphthyl" and insert -- 15-thianaphthyl --.

Signed and Sealed this

Twenty-seventh Day of January, 2004

JON W. DUDAS
*Acting Director of the United States Patent and Trademark Office*